United States Patent
Joshi-Hangal et al.

(10) Patent No.: US 6,828,346 B2
(45) Date of Patent: Dec. 7, 2004

(54) METHODS FOR ADMINISTRATION OF PACLITAXEL

(75) Inventors: Rajashree Joshi-Hangal, Union City, CA (US); Howard Sands, Wilmington, DE (US); Joseph Rubinfeld, Danville, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 10/351,262

(22) Filed: Jan. 23, 2003

(65) Prior Publication Data

US 2003/0191179 A1 Oct. 9, 2003

Related U.S. Application Data

(63) Continuation-in-part of application No. 09/948,133, filed on Sep. 5, 2001, now Pat. No. 6,538,020, which is a continuation of application No. 09/665,890, filed on Sep. 20, 2000, now Pat. No. 6,319,943, which is a continuation of application No. 09/427,153, filed on Oct. 25, 1999, now Pat. No. 6,136,846.

(51) Int. Cl.$^7$ ...................... A61K 31/335; A61K 31/56; A61K 31/34; A61K 31/135
(52) U.S. Cl. ...................... 514/449; 514/171; 514/474; 514/651
(58) Field of Search ................. 514/449, 171, 514/474, 651

(56) References Cited

U.S. PATENT DOCUMENTS

| | | | | |
|---|---|---|---|---|
| 5,504,102 A | * | 4/1996 | Agharkar et al. | 514/449 |
| 5,670,537 A | * | 9/1997 | Canetta et al. | 514/449 |
| 5,681,846 A | * | 10/1997 | Trissel | 514/449 |
| 5,925,776 A | * | 7/1999 | Nikolayev et al. | 554/219 |
| 6,017,948 A | * | 1/2000 | Rubinfeld et al. | 514/449 |
| 6,046,230 A | * | 4/2000 | Chung et al. | 514/499 |
| 6,136,846 A | * | 10/2000 | Joshi-Hangal et al. | 514/449 |
| 2003/0087954 A1 | * | 5/2003 | Palepu et al. | 514/449 |

FOREIGN PATENT DOCUMENTS

| | | | | |
|---|---|---|---|---|
| WO | 98/30205 | * | 7/1998 | A61K/9/107 |
| WO | 99/45918 | * | 9/1999 | A61K/31/335 |
| WO | 00/71163 | * | 11/2000 | A61K/47/22 |
| WO | 00/78247 | * | 12/2000 | A61K/9/20 |

OTHER PUBLICATIONS

Cecil Textbook of Medicine, Goldman et al. (eds.), 21$^{st}$ Ed. vol. 1, published 2000 by W.B. Saunders Co., (PA), pp 1060–1074.*

* cited by examiner

Primary Examiner—Raymond J. Henley, III

(57) ABSTRACT

Methods are provided for using paclitaxel for treating diseases associated with abnormal cell proliferation and angiogenesis. In particular, methods are provided for administration of paclitaxel formulated with vitamin E derivatives such as d-α-tocopherol polyethylene glycol succinate to a cancer patient. By administering to a patient paclitaxel in a vehicle containing a solubilizer other than Cremophor, acute hypersensitivity caused by Cremophor can be avoided and therapeutic index of paclitaxel may also be increased through potentiation of anti-neoplastic effects by the vitamin E derivatives.

48 Claims, 4 Drawing Sheets

FIGURE 1

Table 4

| Group | n | Treatment Regimen ||||| MDS to 1.5 g ± SEM (n) | # Toxic Deaths | # of Survivors | # CR | # PR | # SD/PD |
|---|---|---|---|---|---|---|---|---|---|---|---|---|
| | | Agent | mg/kg | Route | Schedule ||||||||
| 1 | 10 | No Treatment | --- | --- | --- | 11.4 ± 0.8 (10) | 0 | 0 | 0 | 0 | 0 |
| 2 | 10 | Clinical Taxol | 15 | iv | qd x 5 | 24.1 ± 2.1 (10) | 0 | 0 | 0 | 0 | 0 |
| 3 | 10 | Clinical Taxol | 9 | iv | qd x 5 | 21.6 ± 0.4 (10) | 0 | 0 | 0 | 0 | 0 |
| 4 | 10 | Paclitaxel in 5% EC | 20 | iv | qd x 5 | 23.9 ± 1.8 (10) | 0 | 0 | 0 | 0 | 0 |
| 5 | 10 | Paclitaxel in 5% EC | 18 | iv | qd x 5 | 26.5 ± 2.2 (10) | 0 | 0 | 0 | 0 | 0 |
| 6 | 10 | Paclitaxel in 5% EC | 15 | iv | qd x 5 | 24.7 ± 1.4 (10) | 0 | 0 | 0 | 0 | 0 |
| 7 | 10 | Paclitaxel in 5% EVE | 20 | iv | qd x 5 | 34.4 ± 3.0 (6) | 4 | 0 | 0 | 0 | 0 |
| 8 | 10 | Paclitaxel in 5% EVE | 15 | iv | qd x 5 | 29.7 ± 2.5 (9) | 1 | 0 | 0 | 0 | 0 |
| 9 | 10 | Paclitaxel in 5% EVE | 10 | iv | qd x 5 | 23.7 ± 1.5 (9) | 0 | 1 | 1 | 0 | 0 |

FIGURE 2

Table 5

| Group | n | Treatment Regimen | | | | MDS to 1.5 g ± SEM (n) | # Toxic Deaths | # of Survivors | # CR | # PR | # SD/PD |
|---|---|---|---|---|---|---|---|---|---|---|---|
| | | Agent | mg/kg | Route | Schedule | | | | | | |
| 1 | 10 | No Treatment | --- | --- | --- | 16.7 ± 2.5 (9) | 0 | 1 | 1 | 0 | 0 |
| 2 | 10 | Clinical Taxol | 20 | iv | qod x 5 | 32.5 ± 2.7 (7) | 0 | 3 | 2 | 1 | 0 |
| 3 | 10 | Paclitaxel in EC | 20 | iv | qod x 5 | 33.4 ± 4.1 (7) | 1 | 2 | 0 | 0 | 2 |
| 4 | 10 | Paclitaxel in EVE | 20 | iv | qod x 5 | 28.6 ± 1.5 (8) | 0 | 2 | 1 | 1 | 0 |
| 5 | 10 | Paclitaxel in EVE | 15 | iv | qod x 5 | 27.6 ± 0.9 (10) | 0 | 0 | 0 | 0 | 0 |
| 6 | 10 | Paclitaxel in EVE | 10 | iv | qod x 5 | 22.8 ± 1.6 (10) | 0 | 0 | 0 | 0 | 0 |

FIGURE 3

Table 6

| Group | n | Treatment Regimen | | | | Max. Mean % Body | # Toxic Death |
|---|---|---|---|---|---|---|---|
| | | Agent | mg/kg | Route | Schedule | Weight Loss (Day) | (Day) |
| 1 | 5 | 1% PEG300: 4% Vitamin E TPGS in D5W | - | po | qd x 5 | -3.7% (Day 5) | 0 |
| 2 | 5 | 1.25% PEG300: 5% Vitamin E TPGS in D5W | - | po | qd x 5 | -1.7% (Day 4) | 0 |
| 3 | 5 | 1.5% PEG300: 6% Vitamin E TPGS in D5W | - | po | qd x 5 | -2.1% (Day 4 & 13) | 0 |
| 4 | 5 | 1.75% PEG300: 7% Vitamin E TPGS in D5W | - | po | qd x 5 | -3.2% (Day 13) | 0 |
| 5 | 5 | 2% PEG300: 8% Vitamin E TPGS in D5W | - | po | qd x 5 | -3.2% (Day 3) | 0 |
| 6 | 5 | 2.25% PEG300: 9% Vitamin E TPGS in D5W | - | po | qd x 5 | -1.7% (Day 4) | 0 |
| 7 | 5 | 2.5% PEG300: 10% Vitamin E TPGS in D5W | - | po | qd x 5 | -0.8% (Day 5) | 0 |
| 8 | 5 | 5% EtOH in D5W: 5% Vitamin TPGS | - | po | qd x 5 | -2.8% (Day 3) | 0 |
| 9 | 5 | 6% EtOH in D5W: 6% Vitamin TPGS | - | po | qd x 5 | -0.8% (Day 3) | 0 |
| 10 | 5 | 7% EtOH in D5W: 7% Vitamin TPGS | - | po | qd x 5 | -2.2% (Day 3 & 4) | 0 |
| 11 | 5 | 8% EtOH in D5W: 8% Vitamin TPGS | - | po | qd x 5 | -2.5% (Day 5) | 0 |
| 12 | 5 | 9% EtOH in D5W: 9% Vitamin TPGS | - | po | qd x 5 | --- | 0 |

FIGURE 4

Table 7

| Group | n | Agent | mg/kg | Route | Schedule | Max. % Mean Body Wt. Loss (Day) | # Toxic Death (Day) |
|---|---|---|---|---|---|---|---|
| 1 | 5 | 2.5% PEG300: 10% Vit E TPGS in D5W | | po | qd x 5 | --- | 0 |
| 2 | 5 | 3.0% PEG300: 12% Vit E TPGS in D5W | | po | qd x 5 | -11.0% (Day 5) | 0 |
| 3 | 5 | 3.5% PEG300: 14% Vit E TPGS in D5W | | po | qd x 5 | --- | 0 |
| 4 | 5 | 4.0% PEG300: 16% Vit E TPGS in D5W | | po | qd x 5 | --- | 0 |
| 5 | 5 | 4.5% PEG300: 18% Vit E TPGS in D5W | | po | qd x 5 | --- | 1 (Day 15)[a] |
| 6 | 5 | 5.0% PEG300: 20% Vit E TPGS in D5W | | po | qd x 5 | -0.5 % (Day 3 & 5) | 0 |
| 7 | 5 | 5.5% PEG300: 22% Vit E TPGS in D5W | | po | qd x 5 | -0.5 % (Day 3) | 0 |
| 8 | 5 | 6.0% PEG300: 24% Vit E TPGS in D5W | | po | qd x 5 | --- | 0 |
| 9 | 5 | 10% EtOH in D5W:10% Vit E TPGS | | po | qd x 5 | -0.5 % (Day 3) | 1 (Day 2)[a] |
| 10 | 5 | 12% EtOH in D5W:12% Vit E TPGS | | po | qd x 5 | --- | 0 |
| 11 | 5 | 14% EtOH in D5W:14% Vit E TPGS | | po | qd x 5 | --- | 0 |
| 12 | 5 | 16% EtOH in D5W:16% Vit E TPGS | | po | qd x 5 | --- | 0 |

[a] Death appeared to be unrelated to drug toxicity.

METHODS FOR ADMINISTRATION OF PACLITAXEL

CROSS REFERENCE TO RELATED APPLICATIONS

This is a continuation-in-part of U.S. Application entitled "Paclitaxel Formulation", Ser. No. 09/948,133, filed Sep. 5, 2001, now U.S. Pat. No. 6,538,020 which is a continuation of U.S. Application entitled "Oral Formulation For Paclitaxel", Ser. No. 09/665,890, filed Sep. 20, 2000, now U.S. Pat. No. 6,319,943, which is a continuation of U.S. Application entitled "Formulation For Paclitaxel", Ser. No. 09/427,153, filed Oct. 25, 1999, now U.S. Pat. No. 6,136,846. Theses applications are hereby incorporated by reference.

BACKGROUND OF THE INVENTION

1. Field of the Invention

This invention relates to compositions that may be used as pharmaceutical compositions, methods and kits, more particularly to improved pharmaceutical formulations for paclitaxel that include vitamin-E derivatives.

2. Description of Related Art

Paclitaxel is a unique diterpene anticancer compound derived from the bark of the *Taxus brevifolia* (Pacific yew) tree. A crude extract of the bark demonstrated antineoplastic activity in preclinical tumor screening 30 years ago as part of the National Cancer Institute's (NCI's) large-scale screening program. The active component of the extract, paclitaxel, was isolated and described by M. C. Wani et al, *Plant antitumor agents, VI: The isolation and structure of Paclitaxel, a novel antileukemic and antitumor agent from Taxus brevifolia*, J. Am. Chem. Soc. 93:2325–2327 (1971). This document, and all others referred to herein, are incorporated by reference as if reproduced fully below.

In 1979, Schiff and coworkers rekindled interest in the development of paclitaxel by demonstrating its novel mechanism of action. Paclitaxel stabilizes the tubulin polymer and promotes microtubule assembly, rather than inducing microtubule disassembly like the antimicrotubule agents colchicine, vincristine, and vinblastine. This stabilization results in the inhibition of the normal dynamic reorganization of the microtubule network. Encouraging response rates (complete and partial) have been reported in single-agent phase II studies of paclitaxel in breast cancer, previously untreated non-small-cell lung cancer, head and neck cancer, and refractory ovarian cancer.

Unfortunately, paclitaxel is poorly soluble in water (less than 0.01 mg/mL) and other common vehicles used for the parenteral administration of drugs. Certain organic solvents, however, may at least partially dissolve paclitaxel. However, when a water-miscible organic solvent containing paclitaxel at near its saturation solubility is diluted with aqueous infusion fluid, the drug may precipitate.

Solubilization of compounds with surfactants allows for dilution of saturated or near-saturated formulations. Consequently, researchers formulated paclitaxel formulations using 50% Cremophor EL/50% dehydrated alcohol (USP, United States Pharmacopoeia), diluted in NS normal saline or D5W (5% dextrose in water) to a final concentration of 5% Cremophor EL and 5% dehydrated alcohol or less, for the intravenous administration of the drug to humans in early clinical trials. (Cremophor EL; Badische Anilin und Soda Fabrik AG [BASF], Ludwigshafen, Federal Republic of Germany). Paclitaxel for injection concentrate is currently available from Bristol-Myers Squibb Co. (New York, N.Y.) in 30-mg (5-mL) single-dose vials. Each milliliter of formulation contains approximately 6 mg Paclitaxel, 527 mg of Cremophor EL, and 49.7% (vol/vol) dehydrated alcohol. This concentrated formulation must be further diluted with NS, D5W, D5NS (normal saline, 5% dextrose in water and 5% dextrose in normal saline) or D5W-R (Ringer's solution with 5% dextrose in water) prior to administration. It has been noted that the Cremophor/Ethanol formulation of paclitaxel precipitates upon dilution with infusion fluid, and fibrous precipitates formed in some compositions during storage for extended periods of time. Additional information regarding Cremophor formulations of paclitaxel may be found in Agharkar et al., U.S. Pat. No. 5,504,102.

An unexpectedly high incidence of serious hypersensitivity reactions was noted in phase I studies of the paclitaxel/Cremophor formulations. D. M. Essayan et al., *Successful Parenteral Desensitization to Paclitaxel*, J. Allergy and Clin. Immun. 97:42–46 (1996). Studies have shown that the Cremophor EL vehicle induces histamine release and hypotension in dogs within 10 minutes of administration.

In January 1985, the NCI sent a letter to all phase I investigators using paclitaxel, directing them to increase the duration of paclitaxel infusions and to pretreat all subjects with antihistamines (both H-1 and H-2 receptor blockers) and steroids. The incidence of hypersensitivity reactions subsequently decreased. Because the infusion duration was increased and pretreatment medications were added at the same time, it was not possible to determine whether infusion rate or pretreatment was the important factor.

Further studies were carried out in which paclitaxel was administered after premedication with steroids (such as dexamethasone, prednisone and hydrocortisone), antihistamines (such as diphenhydramine), and H-2 receptor blockers (such as cimetidine or ranitidine), and the infusion time was extended to 24 hours in an attempt to eliminate the most serious allergic reactions. See Einzig, et al., *Phase II Trial of Taxol in Patients with Metastatic Renal Cell Carcinoma*, Cancer Investigation, 9:133–136 (1991); A. B. Miller et al., *Reporting Results of Cancer Treatment*, Cancer 47:207–214 (1981). Additional description of premedication techniques may be found in Carretta et al., U.S. Pat. No. 5,670,537.

There are other disadvantages to using Cremophor formulations as well. Polyvinylchloride (PVC) infusion bags and intravenous administration sets usually contain diethylhexylphthalate (DEHP) as a plasticizer to maximize component flexibility. DEHP leaches to some extent into aqueous infusion fluids and blood products that come in contact with PVC materials. Exposure of animals to chronic high doses (more than 100 mg/kg) of DEHP has resulted in toxic effects including growth retardation, liver weight increase, liver damage, testicular atrophy, teratogenicity, and carcinogenicity. Cosolvents and surfactants may increase the amount of plasticizer leached. Waugh and colleagues evaluated the quantities of DEHP extracted from PVC infusion devices by the commercially available paclitaxel formulation. Substantial quantities of DEHP were extracted by all formulation concentrations tested. Therefore, there is a substantial health risk to patients receiving paclitaxel in the commercially available formulation using conventional PVC-containing equipment.

There is therefore a need for improved formulations comprising paclitaxel, methods of treatment using these formulations and kits comprising these formulations, to overcome the stability problems and to alleviate the clinical side effects of conventional paclitaxel formulations as noted above and as known to one of skill in the art.

SUMMARY OF THE INVENTION

The present invention provides new and improved formulations of paclitaxel, methods of manufacturing these formulations, kits containing these formulations and methods of treating cancer patients using these formulations. The new and improved formulations include pharmaceutically acceptable, water miscible solubilizers other than Cremorphor which are believed to have improved long term stability and reduced adverse effects relative to existing formulations.

In one aspect of the present invention, a composition for delivering paclitaxel in vivo is provided, which comprises paclitaxel; a solvent; and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety. The solubilizer is selected such that it does not have a pKa less than about 6. Optionally, the solubilizer does not have a pKa less than about 7, more preferably not less than about 8. By designing the solubilizer to not have any acidic hydrogens, potential destabilization of paclitaxel catalyzed by anionic moieties may be reduced. Upon the addition of water, the solubilizer forms micelles within which the paclitaxel is solubilized in the aqueous solution.

The solubilizer may preferably be an ester ($R_1COOR_2$) derived from a lipophilic acid ($R_1COOH$) that has been esterified with a hydrophilic alcohol ($R_2OH$). Examples of the lipophilic acids ($R_1COOH$) include long chain carboxylic acids such as lauric acid, palmitic acid, stearic acid, oleic acid, linoleic acid, archidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivative, and is most preferably d-α-tocopherol polyethylene glycol succinate (TPGS).

The solvent in the composition may be pharmaceutically acceptable, water miscible organic solvent that can dissolve both paclitaxel and the solubilizer. Examples of suitable solvents include alcohols such as ethanol, propylene glycol and benzyl alcohol; polyalcohols such as polyethylene glycol (PEG); and amides such as 2-pyrrolidone, N-methylpyrrolidone and N,N-dimethyl acetamide.

The concentration of paclitaxel in the composition may preferably range from about 5–20 mg/g, more preferably from about 8–15 mg/g, and most preferably from about 10–13 mg/g.

The concentration of solubilzer in the composition may preferably range from about 40–90%w/w, more preferably from 45–75%w/w and most preferably from 50–60%w/w.

The weight ratio of the solubilizer to the solvent may preferably be between about 90:10–40:50, more preferably between about 70:30–45:55, and most preferably about 50:50.

The weight ratio of paclitaxel to the solubilizer may preferably be between about 1:10–1:100, more preferably about 1:20–1:80, and most preferably about 1:30–1:70.

In a preferred embodiment, the composition further comprises an acidifying agent added to the composition in a proportion such that the composition has a resulting pH between about 3 and 5. The acidifying agent may be an organic acid. Examples of organic acid include ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

Optionally, the solubilizer does not have a hydrogen with a pKa less than about 7, more preferably not less than about 8. By designing the solubilizer to not have any acidic hydrogens, potential destabilization of paclitaxel catalyzed by anionic moieties may be reduced.

The composition may be diluted into aqueous solution by adding saline or other infusion fluid for parenteral administration or intravenous injection.

The composition may optionally be incorporated into a pharmaceutical carrier suitable for oral administration. For example, the composition may be filled into a soft or hard gelatin capsule, or other oral dosage forms. In these oral formulations, polyethylene glycols such as PEG 300 and PEG400 may preferably be used as the solvent for solubilizing paclitaxel, and the concentration of the solvent may preferably be less than about 40%w/w in the finally formed semi-solid or solid composition. These oral formulations may be administered into a host in need thereof, such as a cancer patient.

In another embodiment, a composition is provided which is made by the acts comprising: providing paclitaxel; and combining the paclitaxel with a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety. The solubilizer is selected such that it does not have a pKa less than about 6.

In another aspect of the present invention, a pharmaceutical formulation for delivering paclitaxel in vivo is provided, which comprises water; and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety. The solubilizer is selected such that it does not have a pKa less than about 6.

The solubilizer may preferably be an ester ($R_1COOR_2$) derived from lipophilic acids ($R_1COOH$) that are esterified with a hydrophilic alcohol ($R_2OH$). Examples of the lipophilic acids $R_1COOH$ include long chain carboxylic acids such as lauric acid, palmitic acid, stearic acid, oleic acid, linoleic acid, archidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivatives, and is most preferably d-α-tocopherol polyethylene glycol succinate (TPGS).

The solubilizer contained in both the composition and the pharmaceutical formulation is an amphiphilic ester ($R_1COOR_2$), an amphiphilic amide ($R_1CONR_2$) or an amphiphilic ketone ($R_1COR_2$) which is capable of forming micelle in aqueous solution. Hydrophobic tails ($R_1$) of the solubilizer aggregate with lipophilic paclitaxel while hydrophilic heads ($R_2$) of the solubilizer self-associate in water. Paclitaxel is thus solubized by associating with the hydrophobic tails of the micelles in aqueous solution.

The weight ratio of paclitaxel to the solubilizer may preferably be between about 1:10–1:100, more preferably about 1:20–1:80, and most preferably about 1:30–1:70.

The pharmaceutical formulation or the composition may optionally further include an excipient added to the composition in an amount sufficient to enhance the stability of the composition. Examples of the excipient includes, but are not limited to, cyclodextrin such as α-, β-, and γ-cyclodextrin and modified, amorphous cyclodextrin such as hydroxy-substituted α-, β- and γ-cyclodextrin.

Another pharmaceutical formulation is also provided, which is made by the acts comprising: providing a stock compostion comprising paclitaxel, a solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and combining the composition with an aqueous solution, wherein, upon addition of the aqueous solution, the solubilizer forms micelles within which the paclitaxel is solubilized in the aqueous solution.

One of the advantages of the above-described pharmaceutical formulations and compositions is the use of a non-ionic, amphiphilic solubilizer for paclitaxel. Previously, destabilization of paclitaxel by free carboxylate anion in formulations of Cremorphor occurred. The use of an ester, an amide or a ketone reduces this destabilization. By stabilizing paclitaxel in the composition, the storage shelf life for the composition can be prolonged, while the potency or pharmaceutical activity of the pharmaceutical formulation can be enhanced.

Another advantage of the pharmaceutical formulation is that paclitaxel is entrapped within the micelles formed by the solubilizer. As a result, light-induced damage to paclitaxel may be reduced during the period of infusion.

A further advantage of the pharmaceutical formulation is that the aqueous solution contains paclitaxel-carrying micelles which remain physically and chemically stable. The formulation can be administered intravascularly without undue toxicity from undissolved drug or precipitates of the solubilizer.

In yet another aspect of the present invention, a kit containing a pharmaceutical formulation for delivering paclitaxel in vivo is provided, the pharmaceutical formulation comprising: water and micelles comprising paclitaxel and a pharmaceutically-acceptable, water-miscible solubilizer forming the micelles, the solubilizer having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6.

In yet another aspect of the present invention, a method for administering paclitaxel to a host in need thereof is provided.

In one embodiment, the method comprises: providing a pharmaceutical formulation comprising: water and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and administering the pharmaceutical formulation in a therapeutically effective amount to a host in need thereof.

The method may be used for administering paclitaxel to patients. A wide variety of uses are known for paclitaxel including the treatment of malignant diseases such as cancer including, but not limited to, human ovarian cancer, breast cancer, malignant lymphoma, lung cancer, melanoma, and Kaposi's sarcoma. Other uses of paclitaxel may be developed in the future. The present invention may also intended to be used in conjunction with these future uses of paclitaxel.

In another embodiment, the method comprises: administering to a patient having a disease associated with abnormal cell proliferation and angiogenesis a pharmaceutical formulation containing paclitaxel, vitamin E-TPGS (D-α-tocopheryl polyethylene glycol succinate), and solvent.

According to the embodiment, paclitaxel is solubilized by vitamin E-TPGS in a solvent, such as ethanol and polyethylene glycol (PEG), to form a homogenous composition. A particular example of vitamin E-TPGS is vitamin E-TPGS 1000 (d-α-tocopherol succinate esterified with PEG 1000).

Also according to the embodiment, the pharmaceutical formulation may further comprise an acidifying agent added to the formulation in a proportion such that the formulation has a resulting pH between about 3 and 5. The acidifying agent may be an organic acid including, but not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, including, but not limited to, hydrochloric acid, sulfuric acid, phosphoric acid, and nitric acid. An anhydrous organic acid may preferably be used in a composition that may be further formulated for oral administration, such as incorporation into soft or hard gelatin capsules, tablet or other oral dosage forms.

The amount of acid added to the formulation may be sufficient to adjust the pH of the formulation at preferably between about pH 3–6, more preferably between about pH 3.5–5, and most preferably between about pH 3–4.

The pharmaceutical formulation may optionally further include an excipient added to the composition in an amount sufficient to enhance the stability of the composition, maintain the product in solution, or prevent side effects associated with the administration of the inventive composition. Examples of excipients include but are not limited to, cyclodextrin such as α-, β-, and γ-cyclodextrin and modified, amorphous cyclodextrin such as hydroxy-substituted α-, β-, and γ-cyclodextrin. Cyclodextrins such as Encapsin® from Janssen Pharmaceuticals may be used for this purpose.

The pharmaceutical formulations described above can be used for delivering paclitaxel in vivo via various routes of administration. For example, the formulation may be administered or coadministered with other therapeutic agent(s) orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The formulation may also be administered or coadministered in slow release dosage forms.

In a particular embodiment, the method comprises: administering to the patient a pharmaceutical formulation comprising paclitaxel and vitamin E-TPGS at a dose of 0.1–50 mg/Kg, preferably 1–20 mg/Kg, more preferably 1–10 mg/Kg, and most preferably 2–8 mg/Kg. The administration may be repeated, preferably every two weeks, and more preferably every three weeks. This formulation may be administered parenterally or orally to patient having a disease associated with undesirable or uncontrolled cell proliferation or angiogenesis.

According to the present invention, paclitaxel formulated with vitamin E-TPGS may be administered parenterally at a dosage lower than the current clinical dosage of TAXOL®: 135 mg/m or 9 mg/Kg for an adult, for example, at dose below 100 mg/m$^2$ or 7 mg/Kg. Paclitaxel formulated with vitamin E-TPGS may also be administered to a cancer patient by infusion for 3 hours or a shorter time once every week at a dosage below 100 mg/m$^2$, such as 80 mg/m$^2$.

Optionally, a desensitizer may be administered to the patients in order to reduce any potential anaphylactic or hypersensitive responses such as allergic reactions, pain and suffering. Examples of desensitizer include, but are not limited to, steroids (such as dexamethasone, prednisone and hydrocortisone), antihistamines (such as diphenhydramine), and H-2 receptor blockers (such as cimetidine or ranitidine). The desensitizer is preferably administered to the patient prior to treatment with paclitaxel formulated with vitamin E-TPGS.

Also optionally, cytokines such as granulocyte-colony stimulating factor (G-CSF) may be administered (e.g., by daily subcutaneous injection) to the patient treated with paclitaxel formulated with vitamin E-TPGS, preferably 24 hours after the paclitaxel treatment to ameliorate myelosuppression effects of paclitaxel or to speed up recovery from myotoxicity.

A wide variety of antineoplastic agents may have a therapeutic additive or synergistic effect with paclitaxel formulated with vitamin E-TPGS. Such antineoplastic agents may be hyperplastic inhibitory agents that addictively or synergistically combine with paclitaxel formulated with vitamin E-TPGS to inhibit undesirable cell growth, such as inappropriate cell growth resulting in undesirable benign conditions or tumor growth. Examples of such antineoplastic agents include, but are not limited to, alkylating agents, antibiotic agents, antimetabolic agents, hormonal agents, plant-derived agents, and biologic agents.

Preferable indications that may be treated using paclitaxel formulated with vitamin E-TPGS include those involving undesirable or uncontrolled cell proliferation. Such indications include restenosis (e.g. coronary, carotid, and cerebral lesions), benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

BRIEF DESCRIPTION OF THE DRAWINGS

FIG. 1 shows Table 4 that summarizes results of the treatment of the nude mice with paclitaxel in 5% EVE, 5% EC and Clinical Taxol via i.v. injection.

FIG. 2 shows Table 5 that summarizes results of toxicity studies of the nude mice treated with various paclitaxel formulations via i.v. injection.

FIG. 3 shows Table 6 that summarizes results of toxicity studies of the nude mice treated with various paclitaxel formulations via oral administration.

FIG. 4 shows Table 7 that summarizes results of toxicity studies of the nude mice treated with various paclitaxel formulations via oral administration.

DETAILED DESCRIPTION OF THE INVENTION

The present invention provides compositions, kits and methods for using paclitaxel for treating diseases associated with abnormal cell proliferation and angiogenesis. In particular, methods are provided for administration of paclitaxel formulated with vitamin E derivative to an animal, preferably a human. According to the present invention, administering to a patient paclitaxel in a vehicle containing a solubilizer other than Cremophor avoids adverse effects associated with Cremophor and may confer stronger therapeutic effects on the patient.

1. Compositions of the Present Invention

In the present invention, compositions are provided which are used for delivering paclitaxel in vivo. In one embodiment, the composition comprises paclitaxel, a solvent and a pharmaceutically-acceptable, water-miscible solubilizer selected from the group consisting of solubilizers having the general structures:

$R_1$ COOR$_2$, $R_1$CONR$_2$, and $R_1$COR$_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6. Upon the addition of water, the solubilizer forms micelles within which the paclitaxel is solubilized in the aqueous solution. This composition may be used as a pharmaceutical composition to treat various diseases or conditions, such as those described in Section 6 below.

The composition for paclitaxel is formulated based on a combination of a non-ionic, amphiphilic solubilizer that forms micelles to solubilize paclitaxel in an aqueous solution and a solvent that can dissolve paclitaxel and disperse the solubilizer in the composition to form a homogenous composition.

A pharmaceutical formulation can be formed from the composition by adding an aqueous solution such as water, saline or other infusion fluid. When an aqueous solution is added, hydrophobic tails of the solubilizer aggregate with paclitaxel and entrap paclitaxel within a micelle, thereby solubilizing and stabilizing paclitaxel in the resultant pharmaceutical formulation.

In the composition, the solubilizer is an ester, an amide or a ketone with a pKa less than about 6. As a result, the solubilizer is essentially non-ionic under pH 6 in an aqueous solution. Optionally, the solubilizer may be selected such that the solubilizer does not have a pKa less than about 7, more preferably not less than about 8. Maintaining non-ionicity of the solubilzer is believed to prevent destabilization of paclitaxel catalyzed by anions such as carboxylate. In contrast, the commercially available paclitaxel formulation with 50:50 ethanol: Cremophor contains carboxylate moieties which ionize and may contribute to the decomposition of paclitaxel in the formulation. The present invention employs an amphiphilic ester as the solubilizer in the composition, carboxylate anion-catalyzed decomposition of paclitaxel may be minimized, thereby enhancing the stability and prolonging storage shelf-life of the drug.

The solubilizer $R_1COOR_2$ may preferably be an ester derived from lipophilic acids ($R_1COOH$) that are esterified with hydrophilic alcohol ($R_2OH$). Examples of lipophilic acids ($R_1COOH$) include long chain carboxylic acids such as lauric acid, palmitic acid, stearic acid, oleic acid, linoleic acid, arachidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivative, and most preferably is d-α-tocopherol polyethylene glycol succinate (TPGS).

The solvent in the composition for delivering paclitaxel in vivo may preferably be pharmaceutically acceptable, water miscible, nonaqueous solvent that can dissolve both paclitaxel and the solubilizer. In the context of this invention, these solvents should be taken to include solvents that are generally acceptable for pharmaceutical use, substantially water-miscible, and substantially non-aqueous. Preferably, these solvents do not cause phthalate plasticizes to leach when the solvents are used with medical equipment whose tubing contains phthalate plasticizers. Preferred examples of the pharmaceutically-acceptable, water-miscible, non-aqueous solvents that may be used in this invention include, but are not limited to, N-methyl pyrrolidone (NMP); propylene glycol; polyethylene glycol (e.g. PEG300, PEG400, etc.); ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (s)-(-)-ethyl lactate; acetone; glycerol; alkyl ketones such as methylethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

Most preferred examples of pharmaceutically-acceptable, water-miscible, non-aqueous solvents include alcohols such as ethanol, propylene glycol and benzyl alcohol; polyalcohols such as polyethylene glycol (PEG 300, PEG 400, etc.); and amides such as 2-pyrrolidone, N-methyl-pyrrolidone and N,N-dimethyl acetamide. Additionally, triacetin may also be used as a pharmaceutically-acceptable, water-miscible, non-aqueous solvent, as well as functioning as a solubilizer in certain circumstances.

Pharmaceutical grade paclitaxel suitable for use in this invention may be obtained from a variety of sources, including the National Cancer Institute (Bethesda, Md.). In the context of this invention, paclitaxel is intended to include paclitaxel proper, and paclitaxel derivatives, analogs, metabolites, and prodrugs thereof.

The composition may contain varying amounts of each of the paclitaxel, the pharmaceutically-acceptable, water-miscible solubilizer, solvent, and other ingredients. In a preferred embodiment, the inventive compositions comprise paclitaxel in an amount ranging from about 5–20 mg/g, more preferably from about 8–15 mg/g, and most preferably from about 10–13 mg/g.

In another preferred embodiment, the composition comprises a solubilizer in an amount ranging from about 40–90% w/w, more preferably from 45–75% w/w, and most preferably from 50–60% w/w.

In yet another preferred embodiment, the weight ratio of the solubilizer to the solvent may be between about 90:10–40:50, more preferably between about 70:30–45:55, and most preferably about 50:50.

In yet another preferred embodiment, the weight ratio of paclitaxel to the solubilizer may be between about 1:10–1:100, more preferably about 1:20–1:80, and most preferably about 1:30–1:70.

In yet another preferred embodiment, the composition further comprises an acidifying agent added to the composition in a proportion such that the composition has a resulting pH between about 3 and 5. Adding an acidifying agent to the composition serves to further stabilize the bond to the carbonyl bond of the solubilizer and prevent carbonyl anion-catalyzed decomposition of paclitaxel, if any.

Optionally, the solubilizer does not have a pKa less than about 7, more preferably not less than about 8. By designing the solubilizer not to include a proton doner under physiological conditions, potential destabilization of paclitaxel catalyzed by anionic moieties may be reduced.

The acidifying agent may be an organic acid including, but not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, including, but not limited to, hydrochloric acid, sulphuric acid, phosphoric acid, and nitric acid. An anhydrous organic acid may preferably be used in a composition that may be further formulated for oral administration, such as incorporation into soft or hard gelatin capsules, tablet or other oral dosage forms.

The amount of acid added to the composition may be sufficient to adjust the pH of the composition at preferably between about pH 3–6, more preferably between about pH 3.5–5, and most preferably between about pH 3–4.

The pharmaceutical formulation or the composition may optionally further include an excipient added to the composition in an amount sufficient to enhance the stability of the composition, maintain the product in solution, or prevent side effects associated with the administration of the inventive composition. Examples of excipients include but are not limited to, cyclodextrin such as α-, β-, and γ-cyclodextrin and modified, amorphous cyclodextrin such as hydroxy-substituted α-., β-, and γ-cyclodextrin. Cyclodextrins such as Encapsin® from Janssen Pharmaceuticals may be used for this purpose.

The composition may be incorporated into a pharmaceutical carrier suitable for oral administration. In a preferred embodiment, polyethylene glycols, such as PEG 300 and 400, may be used as the solvent for their capability of solubilizing paclitaxel and forming semi-solid to solid compositions. In this embodiment, the concentration of polyethylene glycol may preferably be less than about 40%w/w in the finally formed composition. The composition may be filled into a soft or hard gelatin capsule, or another suitable oral dosage form with protective or sustained release coatings and orally administered into a host in need thereof, such as a cancer patient.

The types of protective or sustained release coating that may be used include, but are not limited to, ethylcellulose, hydroxypropylmethylcellulose, hydroxypropylcellulose, hydroxyethylcellulose, and esters of methacrylic and ethacrylic acid (Eudragit RL, RS, and NE polymer products, Rohm Pharma, Darmstadt, Germany). The enteric protective materials or coatings may be, for example, cellulose acetate pthalate, hydroxypropylmethylcellulose, ethylvinylacetate pthalate, polyvinylacetate pthalate and esters of methacrylic and ethacrylic acid (Eudragit S, Eudragit L and Eudragit E30D, Rohm Pharma, Darmstadt, Ger.).

Alternatively, the composition may also be diluted into an aqueous solution to form a pharmaceutical formulation by adding saline or other infusion fluid for parenteral administration or intravenous injection. The pharmaceutical formulation will be described in details below.

2. Pharmaceutical Formulations of the Present Invention

In the present invention, pharmaceutical formulations for delivering paclitaxel in vivo are also provided, which comprise water and micelles comprising paclitaxel and a pharmaceutically-acceptable, water-miscible solubilizer forming the micelles, the solubilizer selected from the group consisting of solubilizers having the general structures:

wherein $R_1$ is a hydrophobic $C_3$–$C_{50}$ alkane, alkene or alkyne and $R_2$ is a hydrophilic moiety, the solubilizer being selected such that it does not have a pKa less than about 6.

The pharmaceutical formulation can be used for delivering paclitaxel in vivo, preferably via parenteral administration. Parenteral administration has been the preferred approach for paclitaxel as therapy for systemic malignancies. Unfortunately, the currently available paclitaxel formulation which is based on a combination of ethanol and polyoxyethylated castor oil (Cremorphorg, BASF, Germany) may precipitate when added to an infusion fluid. Cremorphor has been associated with a series of clinical side effects necessitating extensive premedication to desensitize the side effects. By contrast, the formulation of the present invention contains a non-ionic ester solubilizer which forms micelles in aqueous solution to solubilize paclitaxel without causing precipitation, and delivers the drug into the body of a host in need.

Generally, micelles can solubilize otherwise insoluble organic material by incorporating the organic material within their hydrophobic interior. The micelle in a pharmaceutical formulation is an association colloid that displays regions of decreasing water solubility going from the outside of the structure to the inside. Micelles are formed by amphiphilic molecules with both hydrophobic and hydrophilic moieties. In the present invention, the solubilizer is an amphiphilic ester with a hydrophobic tail ($R_1$) and a hydrophilic head ($R_2$). The hydrophobic tail of the solubilizer aggregates with lipophilic paclitaxel to form the interior of the micelle while the hydrophilic head ($R_2$) of the solubilizer self-associates with other hydrophilic heads and faces water outside of the micelle. Paclitaxel which is substantially insoluble in aqueous solution is thus solubilized by micelle formation.

The micelles may preferably be non-ionic, such that the head group region of a micelle resembles a concentrated aqueous solution of solute. A non-ionic head group, e.g. sugar or PEG, becomes hydrated by the aqueous solution and solubilizes the micelle. The non-ionic tail group, e.g. long hydrocarbon chain, aggregates with the lipophilic drug via van der Waals interactions, and occupies a range of areas by changing its extended length, compressing or extending its hydrocarbon chain.

The solubilizer ($R_1COOR_2$) may preferably be an ester derived from lipophilic acids ($R_1COOH$) that are esterified with hydrophilic alcohol ($R_2OH$). Examples of the lipophilic acids ($R_1COOH$) include long chain carboxylic acids such as lauric acid, palmitic acid, stearic acid, oleic acid, linoleic acid, arachidonic acid, and d-α-tocopheryl acid succinate. Examples of hydrophilic alcohols ($R_2OH$) include polyalcohols such as polyethylene glycols (PEG): PEG 300, 400, and 1000. In a preferred embodiment, the solubilizer is a water miscible vitamin E derivative, and most preferably is d-α-tocopherol polyethylene glycol succinate (TPGS).

TPGS is derived from vitamin E by esterification of the acid group of d-α-tocopherol succinate with polyethylene glycol. In particular, the commercially available TPGS 1000 esterified with PEG 1000 (Eastman Chemical Company) is water soluble up to approximately 20 wt % and stable under heat sterilization conditions. In addition, the viscosity of TPGS 1000 appears to be constant and low at concentrations below 20 wt %, a desirable property for a pharmaceutical formulation used in parenteral administration.

Other water miscible, amphiphilic solubilizer derived from d- or dl-α-tocopherol may also be used. For example, d- or dl-α-tocopherol may be esterified by water soluble aliphatic dicarboxylic acid such as malonic, succinic, glutaric, adipic, pimelic and maleic acid to form a salt, which is then further esterified with hydrophiles such as PEG to produce water miscible, amphiphilic solubilizers.

In another preferred embodiment, the weight ratio of paclitaxel to the solubilizer may be between about 1:10–1:100, more preferably about 1:20–1:80, and most preferably about 1:30–1:70.

The pharmaceutical formulation can be used for delivering paclitaxel in vivo, preferably via parenteral or intravenous administration. Since the aqueous formulation contains paclitaxel-carrying micelles which remain physically and chemically stable, this formulation can be administered intravascularly without undue toxicity from undissolved drug or precipitates of the solubilizer and still maintains its pharmacological potency. Further, in this formulation, paclitaxel is entrapped within the micelles formed by the solubilizer, thus light-induced damage to paclitaxel may be reduced during the period of infusion.

In a particular embodiment, the paclitaxel formulation comprises a derivative of vitamin E, vitamin E-TPGS (D-α-tocopheryl polyethylene glycol succinate). In addition, the formulation contains a solvent that can dissolve paclitaxel and disperse vitamin E-TPGS to form a homogenous composition, such as ethanol and polyethylene glycol (PEG).

It is believed that upon the addition of water, vitamin E-TPGS forms micelles within which the paclitaxel is solubilized in the aqueous solution. Prior to administration, for example intravenous (I.V.) infusion, paclitaxel formulated with vitamin E-TPGS can be dispersed or diluted with water, saline or other infusion fluid. When an aqueous solution is added, hydrophobic tails of vitamin E-TPGS (the vitamin E moiety) aggregate with paclitaxel and entrap paclitaxel within a micelle, thereby solubilizing and stabilizing paclitaxel in the resultant pharmaceutical formulation.

The paclitaxel formulated with vitamin E-TPGS can be used for delivering paclitaxel in vivo, for example, via parenteral or intravenous administration. Since the aqueous formulation contains paclitaxel-carrying vitamin E-TPGS micelles which remain physically and chemically stable, this formulation can be administered intravascularly without undue toxicity from undissolved drug or precipitates of the solubilizer and still maintains its pharmacological potency. Further, in this formulation, paclitaxel is entrapped within the micelles formed by vitamin E-TPGS, thus light-induced damage to paclitaxel may be reduced during the period of infusion.

In addition, vitamin E-TPGS is essentially non-ionic under pH 6 in an aqueous solution. Maintaining non-ionicity of the solubilzer is believed to prevent destabilization of paclitaxel catalyzed by anions such as carboxylate. In comparison, the commercially available paclitaxel formulation with 50:50 ethanol: Cremophor contains carboxylate moieties which ionize and may contribute to the decomposition of paclitaxel in the formulation. Thus, by employing an amphiphilic ester as the solubilizer in the composition, carboxylate anion-catalyzed decomposition of paclitaxel may be minimized, thereby enhancing the stability and prolonging storage shelf-life of the drug.

3. Manufacture of Pharmaceutical Compositions

The present invention also provides a method of manufacture of pharmaceutical compositions. In one embodiment, a pharmaceutical composition is made by the acts comprising: providing paclitaxel; and combining the paclitaxel with a pharmaceutically-acceptable, water-miscible solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6.

In one variation of the embodiment, the pharmaceutical composition may be prepared by dissolving paclitaxel in a small quantity of a pharmaceutically-acceptable, water-miscible solvent with moderate agitation. The volume of the pharmaceutical composition is then made up with the solubilizer dissolved in the solvent and other ingredients and mixed thoroughly.

In another variation of the embodiment, where the pharmaceutical composition further comprises excipients, the excipients, such as hydroxypropyl cyclodextrin, may also be dissolved in an aliquot of the pharmaceutically-acceptable, water-miscible solvent. This aliquot may then be mixed with a premixed solution of paclitaxel and solubilizer as described above. The mixed aliquots are then mixed together, and the remaining volume is made up with the solvent, all under moderate agitation.

In yet another variation of the embodiment, where the pharmaceutical composition further comprises an acidifying agent, the acidifying agent, may be added to the premixed solution of paclitaxel and solubilizer as described above and mixed under moderate agitation. Examples of the acidifying agent include organic acids such as ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid, and inorganic acids, such as hydrochloric acid, sulphuric acid, phosphoric acid, and nitric acid. The amount of the acidifying agent may be sufficient to adjust the pH of the final formulation to a desired range after dilution of the pharmaceutical composition with infusion fluid, such as saline.

In another embodiment, a pharmaceutical composition is made by the acts comprising: providing a compostion comprising paclitaxel, a solvent and a pharmaceutically-acceptable, water-miscible solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and combining the composition with an aqueous solution, wherein, upon addition of the aqueous solution, the solubilizer forms micelles within which the paclitaxel is solubilized in the aqueous solution.

A kit containing a pharmaceutical formulation for delivering paclitaxel in vivo is also provided, the pharmaceutical formulation comprising: water and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6.

4. Methods of Administration of Paclitaxel Formulations of the Present Invention A method for administering paclitaxel to a host in need thereof is provided, comprising: providing a pharmaceutical formulation comprising: water and micelles comprising paclitaxel and a pharmaceutically-acceptable, water-miscible solubilizer forming the micelles, the solubilizer selected from the group consisting of solubilizers having the general structures:

$R_1COOR_2$, $R_1CONR_2$, and $R_1COR_2$, wherein $R_1$ is a hydrophobic $C_3$–$C_{50}$ alkane, alkene or alkyne and $R_2$ is a hydrophilic moiety, the solubilizer being selected such that it does not have a pKa less than about 6; and administering the pharmaceutical formulation in a therapeutically effective amount to a host in need thereof.

The pharmaceutical formulations according to the invention may be administered in any medically suitable manner, preferably parenterally or orally, more preferably parenterally, and still more preferably intravenously. The pharmaceutical formulation may be prepared by diluting the a composition as described in Section 1 with sterile water, normal saline, D5W, Ringer's solution or other equivalent infusion liquids.

Dilutions of the composition may preferably range from about 5:1 to about 1:10 v/v of the composition to the diluting infusion liquids. The dilutions may also be appropriately adjusted according to specific treatment schemes adopted by clinicians. The ratio of v/v in this context refers to the ratio of the volume of the composition before dilution with the infusion fluids to the total volume of the pharmaceutical formulation following dilution with the infusion fluid. Additionally, the pharmaceutical may be administered in a bolus fashion.

When administering therapeutic agents such as paclitaxel, a highly stable formulation is desirable. Chemical stability of a formulation generally refers to the amount of chemical degradation of a particular agent in the formulation. Chemical stability of a pharmaceutical formulation depends upon the amount of chemical degradation of the active pharmaceutical ingredient in that preparation. Commonly, stability analysis of a pharmaceutical preparation, such as a liquid parenteral product, may be performed under accelerated temperature conditions, such as in a 50° C. oven. For example, stability data for 50° C. for one month can give assurance of stability for a minimum of two years at room temperature. The predictive nature of accelerated stability studies at elevated temperatures is governed by the Arrhenius equation.

Developing formulations of acceptable chemical stability may be important, especially in cases where the composition comprises a cytotoxic drug like the paclitaxel. Physicians will find products which require determining the exact amount of paclitaxel present before using the products undesirable. Additionally, regulatory requirements may specify minimum stability requirements. Therefore, discovery of variables that impact stability is a useful step in development of new pharmaceutical formulations.

Acceptable stability is well understood by one of skill to mean chemical stability that is sufficient for the material to be well accepted in clinical use, that definition being used herein. In a preferred embodiment, the chemical stability of paclitaxel in a 50° C. oven over four weeks is greater than about 85%. In a more preferred embodiment, the chemical stability of paclitaxel in a 50° C. oven over four weeks is greater than about 90%. In a still more preferred embodiment, the chemical stability of paclitaxel in a 50° C. oven over four weeks is greater than about 93%. In a most preferred embodiment, the chemical stability of paclitaxel in a 50° C. oven over four weeks is greater than about 96%.

The paclitaxel formulations as described above can be used for delivering paclitaxel in vivo via various routes of administration. For example, the formulation may be administered or coadministered with other therapeutic agent(s) orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The formulation may also be administered or coadministered in slow release dosage forms.

Since the discovery of the anti-cancer activity of paclitaxel, parenteral administration has been the preferred approach for paclitaxel as therapy for systemic malignancies. Unfortunately, the currently available paclitaxel formulation which is based on a combination of ethanol and polyoxyethylated castor oil (Cremophor®, BASF, Germany) sometimes precipitate when added to an infusion fluid. Cremophor has been associated with a series of clinical side effects necessitating extensive premedication to desensitize the side effects. Paclitaxel formulated with a non-ionic ester solubilizer such as vitamin E-TPGS which forms micelles in aqueous solution should be able to solubilize paclitaxel without causing precipitation, and delivers the drug into the body of a host in need without the clinical side effects associated with Cremophor.

The present invention provides methods for administering to a patient in need thereof paclitaxel formulated with vitamin E derivatives, such as vitamin E-TPGS. In one embodiment, the method comprise: administering to the patient a pharmaceutical formulation comprising paclitaxel and vitamin E-TPGS at a dose of 0.1–50 mg/Kg, preferably 1–20 mg/Kg, more preferably 1–10 mg/Kg, and most preferably 2–8 mg/Kg. The administration may be repeated, preferably every two weeks, and more preferably every three weeks. This formulation may administered parenterally or orally to patient having a disease associated with undesirable or uncontrolled cell proliferation or angiogenesis.

In a preferred embodiment, paclitaxel formulated with vitamin E-TPGS is administered parenterally to a patient in need thereof. Since the antitumor activity of paclitaxel can be potentiated by vitamin E-TPGS as shown below in the "EXAMPLE" section, lower dosage of paclitaxel may be needed to achieve the same therapeutic effect as that of paclitaxel formulated with Cremophor (TAXOL®) at higher dosages. For example, the current clinical dosing schedule of TAXOL® is three-hour infusion for breast cancer at 175 mg/m$^2$ (about 13 mg/Kg for an adult weighing 70 Kg) every 3 weeks, ovarian cancer at 135 mg/m$^2$ (about 9 mg/Kg) or 175 mg/m$^2$ every 3 weeks, AIDS-related Kaposi's sarcoma (KS) at 135 mg/m$^2$ (about 9 mg/Kg) or 175 mg/m$^2$ every 3 weeks. According to the present invention, paclitaxel formulated with vitamin E-TPGS may be administered parenterally at a dosage lower than 135 mg/m$^2$ or 9 mg/Kg for an adult, for example at dose below 100 mg/m$^2$ or 7 mg/Kg.

In addition, paclitaxel formulated with vitamin E-TPGS may be better tolerated by patient due to lack of hypersensitivity caused by Cremophor, and therefore could be administered in a shorter infusion time more frequently at a lower dosage than TAXOL®. Long infusion time, such as a 24-hr infusion, requires patients to stay in a hospital and be monitored for the entire period of infusion, thus increasing patients' inconvenience and expenses. Infusion of paclitaxel in a shorter period of time, e.g., 3 hours, would allow for patients to be treated on an out-patient basis, thereby reducing the cost and discomfort of patients. Moreover, shorter duration of infusion and lower dosage of paclitaxel may cause less myelosuppression, thus reducing the incidence of infections and fever episodes. For example, paclitaxel formulated with vitamin E-TPGS may be administered to a cancer patient by infusion for 3 hours or a shorter time once every week at a dosage below 100 mg/m$^2$, such as 80 mg/m$^2$.

Although paclitaxel formulated with vitamin E-TPGS should not cause Cremophor associated hypersensitivity in patients, a desensitizer may optionally be administered to the patients in order to reduce any potential anaphylactic or hypersensitive responses such as allergic reactions, pain and suffering. Examples of desensitizer include, but are not limited to, steroids (such as dexamethasone, prednisone and hydrocortisone), antihistamines (such as diphenhydramine), and H-2 receptor blockers (such as cimetidine or ranitidine). The desensitizer or a combination of desensitizers is preferably administered to the patient prior to treatment with paclitaxel formulated with vitamin E-TPGS.

In addition, cytokines such as granulocyte-colony stimulating factor (G-CSF) may optionally administered (e.g., by daily subcutaneous injection) to the patient treated with paclitaxel formulated with vitamin E-TPGS, preferably 24 hours after the paclitaxel treatment to ameliorate myelosuppression effects of paclitaxel or to speed up recovery from myotoxicity.

When administered by infusion, infusion fluid containing paclitaxel formulated with vitamin E-TPGS may be prepared by dilution with sterile water, normal saline, D5W, Ringer's solution or other equivalent infusion liquids.

Dilutions of the composition may preferably range from about 5:1 to about 1:10 v/v of the composition to the diluting infusion liquids. The dilutions may also be appropriately adjusted according to specific treatment schemes adopted by clinicians. The ratio of v/v in this context refers to the ratio of the volume of the composition before dilution with the infusion fluids to the total volume of the paclitaxel formulation following dilution with the infusion fluid. Additionally, paclitaxel formulated with vitamin E-TPGS may be administered in a bolus fashion.

When administering therapeutic agents such as paclitaxel, a highly stable formulation is desirable. Chemical stability of a formulation generally refers to the amount of chemical degradation of a particular agent in the formulation. Chemical stability of a pharmaceutical formulation depends upon the amount of chemical degradation of the active pharmaceutical ingredient in that preparation. Commonly, stability analysis of a pharmaceutical preparation, such as a liquid parenteral product, may be performed under accelerated temperature conditions, such as in a 50° C. oven. For example, stability data for 50° C. for one month can give assurance of stability for a minimum of two years at room temperature. The predictive nature of accelerated stability studies at elevated temperatures is governed by the Arrhenius equation.

Acceptable stability is well understood by one of skill to mean chemical stability that is sufficient for the material to be well accepted in clinical use, that definition being used herein. As shown below in the "EXAMPLE" section, the chemical stability of paclitaxel formulated with vitamin E-TPGS in a 50° C. oven over four weeks is greater than 95% (Table 2). In addition, paclitaxel at 12.5 mg/g in 50:50 ethanol: vitamin E-TPGS did not cause precipitation within 24 hours of dilution with normal saline (Table 3).

5. Combination Therapy of Paclitaxel with Other Antineoplastic Agents

A wide variety of antineoplastic agents may have a therapeutic additive or synergistic effect with paclitaxel formulations of the present invention. Such antineoplastic agents may be hyperplastic inhibitory agents that addictively or synergistically combine with the inventive paclitaxel formulation to inhibit undesirable cell growth, such as inappropriate cell growth resulting in undesirable benign conditions or tumor growth. Examples of such antineoplastic agents include, but are not limited to, alkylating agents, antibiotic agents, antimetabolic agents, hormonal agents, plant-derived agents, and biologic agents.

The alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including the inventive paclitaxel formulation and the alkylating agent may have therapeutic synergistic effects on cancer and reduce sides affects associated with these chemotherapeutic agents.

The antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interferes with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including the inventive paclitaxel formulation and the antibiotic agent may have therapeutic synergistic effects on cancer and reduce sides affects associated with these chemotherapeutic agents.

The antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including the inventive paclitaxel formulation and the antimetabolic agent may have therapeutic synergistic effects on cancer and reduce sides affects associated with these chemotherapeutic agents.

The hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including the inventive paclitaxel formulation and the hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin (e.g., 20(S)-camptothecin, 9-nitro-20(S)-camptothecin and 9-amino-20(S)-camptothecin). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including the inventive paclitaxel formulation and the plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immunomodulating proteins such as cytokines, monoclonal antibodies against tumor antigens, tumor suppressor genes, and cancer vaccines. Combination therapy including the inventive paclitaxel formulation and the biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon α (IFN-α) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with the inventive paclitaxel formulation include, but are not limited to, interleukin 2 (IL-2), and interleukin 4 (IL-4), interleukin 12 (IL-12).

Interferon α include more than 23 related subtypes with overlapping activities, all of the IFN-α subtypes within the scope of the present invention. IFN-α has demonstrated activity against many solid and hematologic malignancies, the later appearing to be particularly sensitive. Examples of interferons that may be used in conjunction with paclitaxel formulated with vitamin E-TPGS include, but are not limited to, interferon α, interferon β (fibroblast interferon) and interferon γ (fibroblast interferon).

Other cytokines that may be used in conjunction with paclitaxel formulated with vitamin E-TPGS include those cytokines that exert profound effects on hematopoiesis and immune functions. Examples of such cytokines include, but are not limited to erythropoietin (epoietin a), granulocyte-CSF (filgrastin), and granulocyte, macrophage-CSF (sargramostim). These cytokines may be used in conjunction with CPT to reduce chemotherapy-induced myelopoietic toxicity.

Other immuno-modulating agents other than cytokines may also be used in conjunction with CPT to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN) (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including paclitaxel formulated with vitamin E-TPGS and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20+ pre-B and mature B cells. RITUXAN® is used as single agent for the treatment of patients with relapsed or refractory low-grade or follicular, CD20+, B cell non-Hodgkin's lymphoma. Combination therapy including paclitaxel formulated with vitamin E-TPGS and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including the inventive paclitaxel formulation and tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to teh tumor cell, TAAs provide targets for the immune system to recognize and cause their destruction. Example of TAAs include, but are not limited to gangliosides (GM2), prostate specific antigen (PSA), α-fetoprotein (AFP), carcinoembryonic antigen (CEA) (produced by colon cancers and other adenocarcinomas, e.g. breast, lung, gastric, and pancreas cancer), melanoma associated antigens (MART-1, gp100, MAGE 1,3 tyrosinase), papillomavirus E6 and E7 fragments, whole cells or portions/lysates of autologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believed to reduce tumor-induced suppression when given in low doses.

A combination therapy including paclitaxel formulated with vitamin E-TPGS and cancer vaccines may have therapeutic synergistic effects on tumors, which would potentially reduce the dosage of paclitaxel needed for effective treatment. Thus, side effects associated with non-specific cytotoxicity due to high doses of chemotherapeutic agent can be reduced.

6. Indications for Treatment with the Inventive Paclitaxel Formulation

Preferable indications that may be treated using the inventive paclitaxel formulation include those involving undesirable or uncontrolled cell proliferation. Such indications include restenosis (e.g. coronary, carotid, and cerebral lesions), benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, gioblastoma multiforma, leukemias, lymphomas, malignant melanomas, epidermoid carcinomas, and other carcinomas and sarcomas.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrom), endometriosis, psoriasis, diabetic retinopaphy, and other ocular angiogenic diseases such as retinopathy of prematurity (retrolental fibroplastic), macular degeneration, corneal graft rejection, neroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanim of various angiogenic factors, including elements of the inflammatory response, such as leukocytes, platelets, cytokines, and eicosanoids, or unidentified plasma constituents have yet to be revealed.

In another embodiment of the present invention, a method is provided for treating diseases associated with undesired and uncontrolled angiogenesis. The method comprises administering to a patient suffering from uncontrolled angiogenesis a therapeutically effective amount of the inventive paclitaxel formulation, such that formation of blood vessels is inhibited. The particular dosage of paclitaxel formulated with vitamin E-TPGS requires to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the inventive paclitaxel formulation may be used to treat a variety of diseases associated with uncontrolled angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disese, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment of the present invention, a method is provided for treating chronic inflammatory diseases associated with uncontrolled angiogenesis. The method comprises administering the inventive paclitaxel formulation to a patient suffering from a chronic inflammatory disease associated with uncontrolled angiogenesis a therapeutically effective amount of the inventive paclitaxel formulation, such that formation of blood vessels is inhibited. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the inventive paclitaxel formulation alone or in conjunction with other anti-inflammatory agents may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rhematoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the inventive paclitaxel formulation should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by paclitaxel formulated with vitamin E-TPGS should reduce the influx of inflammatory cells and prevent the lesion formation.

Sarcoidois, another chronic inflammatory disease, is characterized as a multisystem granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the inventive paclitaxel formulation to inhibit angionesis, such granulomas formation can be inhibited. Psoriasis, also a chronic and recurrent inflammatory disease, is characterized by papules and plaques of various sizes. Treatment using the inventive paclitaxel formulation alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using paclitaxel formulated with vitamin E-TPGS alone or in conjunction with other anti-RA agents should prevent the formation of new blood vessels necessary to maintain the chronic inflammation and provide the RA patient relief from the symptoms.

The inventive paclitaxel formulation may also be used in conjunction with other anti-angiogenesis agents to inhibit undesirable and uncontrolled angiogenesis. Examples of anti-angiogenesis agents include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,1-3,4-dehydroproline, thiaproline], $\alpha$, $\alpha$-dipyridyl, $\beta$-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), $\beta$-1-anticollagenase-serum, $\alpha$-2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359–1364.

It will be apparent to those skilled in the art that various modifications and variations can be made in the compositions, kits, and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLE

Example 1

Paclitaxel (10 mg) was dissolved in ethanol. Vitamin E TPGS (VTPGS, 700 mg, Eastman Chemical Company) was melted at 50° C. and dissolved separately in ethanol in a ratio of 3:1, respectively. The paclitaxel and VTPGS solutions were mixed and ethanol was added to the solution to a final amount of 300 mg, resulting in a 7:3 weight ratio of VTPGS to ethanol. Anhydrous ascorbic acid (5 mg) was then added to the mixture. The resultant stock solution (08-A) appears clear and yellow in color. The total volume of the stock solution was 25 mL.

Aliquots of the stock solution (08-A) was transferred into vials at 5 mL/vial, and incubated at 4° C., 25° C., 40° C. and 50° C. respectively for periods of time as listed in Tables 1A, 1B, 1C and 1D. Samples were taken at one week or predetermined intervals and tested for chemical stability. The stability testing was performed using an HPLC method. A LC-F (penta-fluorophenyl bonded phase) 5 $\mu$m, 100 Å pore size, 4.6×250 mm column was used. A UV detector set at 227 nm was used. The mobile phase was made up of a 37:58:5 mixture of ACN:Water:MeOH (containing 1 mL/L of $H_3PO_4$). The flow rate was 1.2 mL/minute. The diluent used was acidic methanol (MeOH containing 0.1% acetic acid). The sample concentration was 0.01 mg/mL. The injection volume was 20 $\mu$l. The retention time was 14.5 minutes. The results are shown in Tables 1A, 1B, 1C and 1D.

One milliliter of the stock solution (08-A) was diluted to 5.0 mL with 0.9% NaCl and observed for precipitation at room temperature for a period of at least 24 hr. The diluted solution had a pH of about 4. The formulation did not show any signs of precipitation after over 24 hrs, Example 2

Paclitaxel (10 mg) was dissolved in ethanol. Vitamin E TPGS (VTPGS, 600 mg) was melted at 50° C. and dissolved separately in ethanol in a ratio of 3:1, respectively. The paclitaxel and VTPGS solutions were mixed and ethanol was added to the solution to a final amount of 400 mg, resulting in a 6:4 weight ratio of VTPGS to ethanol. Anhydrous ascorbic acid (5 mg) was then added to the mixture. The resultant stock solution (08-B) appears clear and yellow in color. The total volume of the stock solution was 25 mL.

Aliquots of the stock solution (08-B) was transferred into vials at 5 mL/vial, and incubated at 4° C., 25° C., 40° C. and 50° C. respectively for periods of time as listed in Tables 1A, 1B, 1C and 1D. Samples were taken at one week or predetermined intervals and tested for chemical stability of paclitaxel. The stability testing was performed using the method outlined in Example 1. The results are shown in Tables 1A, 1B, 1C and 1D.

One milliliter of the stock solution (08-B) was diluted to 5.0 mL with 0.9% NaCl and observed for precipitation at room temperature for a period of at least 24 hr. The diluted solution had a pH of about 4. The formulation did not show any signs of precipitation after over 24 hr or greater.

Example 3

Paclitaxel (10 mg) was dissolved in ethanol. Vitamin E TPGS (VTPGS, 500 mg) was melted at 50° C. and dissolved separately in ethanol in a ratio of 3:1, respectively. The paclitaxel and VTPGS solutions were mixed and ethanol was added to the solution to a final amount of 500 mg, resulting in a 5:5 weight ratio of VTPGS to ethanol. Anhydrous ascorbic acid (5 mg) was then added to the mixture. The resultant stock solution (08-C) appears clear and yellow in color. The total volume of the stock solution was 25 mL.

Aliquots of the stock solution (08-C) was transferred into vials at 5 mL/vial, and incubated at 4° C., 25° C., 40° C. and 50° C. respectively for periods of time as listed in Tables 1A, 1B, 1C and 1D. Samples were taken at one week intervals and tested for chemical stability of paclitaxel. The stability testing was performed using the method outlined in Example 1. The results are shown in Tables 1A, 1B, 1C and 1D.

One milliliter of the stock solution (08-C) was diluted to 5.0 mL with 0.9% NaCl and observed for precipitation at room temperature for a period of at least 24 hr. The diluted solution had a pH of about 4. The formulation did not show any signs of precipitation after over 24 hrs.

TABLE 1A

| Time (month at 4° C.) | 08-A | 08-B | 08-C |
|---|---|---|---|
| | (% Paclitaxel Remaining) | | |
| 0 | 100 | 100 | 100 |
| 1 | 99 | 102 | 103 |
| 3 | 103 | 103 | 104 |

TABLE 1B

| Time (month at 25° C.) | 08-A | 08-B | 08-C |
|---|---|---|---|
| | (% Paclitaxel Remaining) | | |
| 0 | 100 | 100 | 100 |
| 1 | 99 | 99 | 101 |
| 2 | 98 | 99 | 101 |
| 3 | 101 | 102 | 104 |

TABLE 1C

| Time (week at 40° C.) | 08-A | 08-B | 08-C |
|---|---|---|---|
| | (% Paclitaxel Remaining) | | |
| 0 | 100 | 100 | 100 |
| 2 | 100 | 101 | 101 |
| 4 | 97 | 98 | 100 |
| 12 | 102 | 103 | 104 |

TABLE 1D

| Time (week at 50° C.) | 08-A | 08-B | 08-C |
|---|---|---|---|
| | (% Paclitaxel Remaining) | | |
| 0 | 100 | 100 | 100 |
| 1 | 98 | 100 | 101 |
| 2 | 100 | 101 | 100 |
| 3 | 97 | 98 | 100 |
| 4 | 96 | 100 | 101 |

Example 4

Chemical and physical stability of the paclitaxel formulation following dilution with normal saline was determined at certain time points after the dilution. Table 2 lists percentages of paclitaxel at indicated time points for a period of 24 hr. after 1:10 dilution of two paclitaxel formulations: paclitaxel at 10 mg/g in 50:50 ethanol: vitamin E TPGS, and paclitaxel at 12.5 mg/g in 50:50 ethanol: vitamin E TPGS.

TABLE 2

| Time (hr) | % Paclitaxel remaining |
|---|---|
| Paclitaxel (10.06 mg/g), at 1:10 dilution (1.01 mg/g) | |
| 0 | 99.74 |
| 2 | 99.73 |
| 4 | 99.44 |
| 8 | 99.55 |
| 24 | 99.16 |
| Paclitaxel (12.44 mg/g), at 1:10 dilution (1.24 mg/g) | |
| 0 | 99.96 |
| 2 | 99.81 |
| 4 | 99.54 |
| 8 | 99.17 |
| 24 | 99.61 |

Table 3 lists observation of precipitation at indicated time points after dilution of the paclitaxel formulation according to the present invention with normal saline at indicated ratios. The paclitaxel formulation has paclitaxel at 12.5 mg/g in 50:50 ethanol: vitamin E TPGS.

TABLE 3

| Dilution Ratio | Precipitation after (hr) | | | | |
|---|---|---|---|---|---|
| | 0 | 24 | 32 | 47 | 71 |
| 1:5 | None | None | Yes | Yes | Yes |
| 1:6 | None | None | Yes | Yes | Yes |
| 1:7 | None | None | Yes | Yes | Yes |
| 1:8 | None | None | None | Yes | Yes |
| 1:9 | None | None | None | None | Yes |
| 1:10 | None | None | None | None | Yes |

Example 5

Antineoplastic Efficacy of Paclitaxel

The therapeutic efficacy of paclitaxel formulated according to the present invention was determined based on growth of human tumor xenografts in nude mice, and compared with that of paclitaxel formulations containing Cremophor.

Paclitaxel was dissolved in 100% ethanol. Addition of an equal weight of vitamin E-TPGS (D-α-tocopheryl polyethylene glycol 1000 succinate) and ten-fold (10×) dilution with D5W (5% dextrose in water at pH 4.8) gave final concentration of 1.0–2.0 mg/ml paclitaxel in D5W containing 5% ethanol and 5% vitamin E-TPGS. This vehicle is designated as "5% EVE".

Paclitaxel formulations containing Cremophor were also prepared. Paclitaxel from the same source as the one used for the vitamin E-TPGS formulation above was dissolved in 50% ethanol:50% Cremophor® EL (Cremophor) and diluted 10-fold with D5W to give final paclitaxel concentrations of 1.5–2.0 mg/ml in 5% ethanol and 5% Cremophor. This vehicle is designated as "5%EC".

Clinical TAXOL® (paclitaxel 6.0 mg/ml in 50% ethanol and 50% Cremophor, designated as "Clinical Taxol" herein after) was obtained from Bristol-Myers Squibb and diluted with D5W to give two final dosing solutions: a) 1.5 mg/ml paclitaxel, 12.5% ethanol, 12.5% Cremophor; and b) 0.9 mg/ml paclitaxel, 7.5% ethanol, 7.5% Cremophor.

Female athymic nude mice ((NCr)-nufBr, Taconic Farms, Inc.) were implanted subcutaneously with an SKMES non-small cell lung carcinoma fragment (1 mm$^3$) in the flank of each mouse. When the neoplasms reached the 60–120 mg size range, the mice were sorted into different treatment groups on Day 1 such that the group tumor sizes ranged from 85.0 mg–86.3 mg. Estimated tumor weight was calculated using the formula:

$$\text{Tumor Weight (mg)} = \frac{w^2 \times l}{2}$$

where w=width and l=length in mm of an SKMES carcinoma.

The tumor growth delay (TGD) method was used to assess efficacy. Each animal was euthanized as a "cancer death" when its SKMES neoplasm reached a size of 1.5 g. Mean Day of Survival (MDS) values for all groups were based on the calculated day of death of each mouse, which is given by the formula:

Time to endpoint (calculated) =

$$\text{Time to exceed endpoint (observed)} - \frac{Wt_2 - \text{endpoint weight}}{\frac{Wt_2 - Wt_1}{D_2 - D_1}}$$

where:

Time to exceed endpoint (observed)=number of days it takes for each tumor to grow past the endpoint (cut-off) size. This is the day the animal is euthanized as a cancer death.

$D_2$=day animal is euthanized.

$D_1$=last day of caliper measurement before tumor reaches the endpoint.

$Wt_2$=tumor weight (mg) on D2

$Wt_1$=tumor weight (mg) on D1.

Endpoint weight=predetermined "cut-off" tumor size for the model being used.

The TGD values, which represent treatment-effected extension of survival time, were calculated from $MDS_{treated}$–$MDS_{control}$, the difference in MDS value for a given treatment groups and the MDS value for SKMES carcinoma-bearing mice that received no treatment.

At the termination of the experiment, treatment responses in survivors were classified as either complete tumor regression (CR), partial tumor regression (PR), or progressive/stable disease (PD/SD). A CR response indicates the absence of measurable tumor. In a PR response, the final tumor weight is smaller than on Day 1. In a PD/SD response, the therapy decreased the rate of neoplastic growth to such an extent that the tumor size did not reach the 1.5-g end point weight by the termination of the study.

To access toxicity of the formulations tested, animals were weighed twice weekly during the study. They were examined frequently for clinical signs of any adverse, drug-related side effects. The maximum tolerated dose (MTD) of the paclitaxel formulation of the present invention was measured in these nude mice. As defined by the National Cancer Institute (NCI), MTD is the dose associated with no more than one death among ten treated mice and less than 20% mean body-weight loss.

The unpaired t-test and Mann-Whitney U test (analyzing means and medians, respectively) were used to determine the statistical significance of any difference in survival time between a treatment group and the control group, and among different treatment groups. All analyses for statistical significance were conducted at P level of 0.05 (two-tailed). Prism (GraphPad) version 3 was used for the statistical analyses and graphic presentation.

1) Treatment with Paclitaxel by I.V. Injection on a Daily Dosing Schedule

On Day 1, the nude mice were matched into 9 groups of 10 animals and each of the paclitaxel formulations prepared above was administered at various doses (specified in Table 4 shown in FIG. 1) on Day 1 by I.V. injection following a qd×5 schedule (1 dose daily for 5 days). The I.V. injections delivered volumes of 0.20 ml per 20-g mouse and were body-weight adjusted. The tumor control group received no treatment. Tumor dimensions were measured twice weekly until the experiment was terminated on Day 44.

Results of the treatment of the nude mice with paclitaxel in 5% EVE, 5% EC and Clinical Taxol are summarized in Table 4 shown in FIG. 1, including MDS values and numbers of toxic deaths, survivors, CR, PR and SD/PD for each group of mice.

As shown in Table 4 in FIG. 1, paclitaxel formulated with 5% EVE has higher antineoplastic efficacy than that of paclitaxel formulated with 5% EC and Clinical Taxol. Treatment of the SKMES lung carcinoma xenografts in athymic mice with Paclitaxel in 5% EVE at 20, 15, 10 mg/kg, resulted in MDS values of 34.4, 29.7, and 23.7 days, causing TGD of 23.1, 18.3, and 12.3 days, respectively.

In contrast, treatment of the same type of nude mice with Paclitaxel in 5% EC and in Clinical Taxol resulted in lower TGD values, i.e., shorter survival time of the mice. For example, treatment at a dose of 15 mg/kg paclitaxel in 5% EVE yielded TGD of 18.3 days, whereas TGD of the treatments with paclitaxel in 5% EC and in Clinical Taxol are 12.5 and 12.7, respectively. Thus, treatment with paclitaxel in the 5% EVE formulation caused an additional extension of survival of almost 5 days.

According to this study, cytotoxic activity of paclitaxel was potentiated more by vitamin E-TPGS than by Cremophor. It was observed that paclitaxel in 5% EVE caused transient partial tumor regression to sizes below that of Day 1 in 5/6 mice at the high dose (20 mg/kg), in 7/9 mice at the intermediate dose (15 mg/kg), and in 3/9 at the low dose (10 mg/kg). Interestingly, treatment with low dose of paclitaxel in 5% EVE resulted in not only survival of a mouse at the termination of the experiment at Day 44, but also complete regression of the tumor implanted into this mouse.

By contrast, treatment with Clinical Taxol only resulted in tumor growth delay, but no transient partial tumor regressions and no 44-day survivors, while paclitaxel in 5% EC formulation caused only 1/10 transient partial regression at the high dose (20 mg/kg), 2/10 at the intermediate dose (18 mg/kg), and 1/10 at the low dose (15 mg/kg), and no 44-day survivors. These results indicate that the formulation of paclitaxel according to the present invention has higher antineoplastic efficacy than that of paclitaxel formulated with Cremophor.

It is noted that the treatment regimen described above, i.e., 1 dose daily for consecutive 5 days (qdx5), was rather harsh and was designed to challenge the mice with maximum tolerated doses (MTD). According to the NCI's definition of MTD, for paclitaxel in 5% EVE the MTD is estimated to be about 15 mg/kg.

2) Treatment with Paclitaxel by I.V. Injection on an Alternate-Day Dosing Schedule To further test the antineoplastic efficacy of paclitaxel in various formulations containing vitamin E-TPGS or Cremophor, a treatment regimen that is less harsh than that (qdx5) described in Section 1) above was adopted. The nude mice bearing SKMES lung carcinoma xenografts were treated with the paclitaxel formulations by I.V. injection on a 5 dose alternate-day schedule (qodx5, i.e., 1 dose every other day with 5 doses total).

On Day 1, the nude mice were matched into 6 groups of 10 animals and each of the paclitaxel formulation prepared above, paclitaxel in 5% EVE or 5% EC, and Clinical Taxol, was administered at various doses (specified in Table 5 shown in FIG. 2) on Day 1 by I.V. injection following a qodx5 schedule. The I.V. injections delivered volumes of 0.20 ml per 20-g mouse and were body-weight adjusted. The tumor control group received no treatment. Tumor dimensions were measured twice weekly until the experiment was terminated on Day 61.

Results of the treatment of the nude mice with the paclitaxel formulations are summarized in Table 5, including MDS values and numbers of toxic deaths, survivors, CR, PR and SD/PD for each group of mice.

As shown in Table 5, when administered via I.V. injection, paclitaxel in 5% EVE at a dose of 20 mg/kg is well tolerated by the mice. No toxic death was observed for the 5% EVE treatment groups, with 1 death for the group treated with 20 mg/kg paclitaxel in 5% EC.

As also shown in Table 5, paclitaxel formulated with 5% EVE has a antineoplastic efficacy comparable to that of paclitaxel formulated with Cremophor. Treatment with paclitaxel in 5% EVE at a dose of 20 mg/kg produced 2 survivors with 1 CR and 1 PR response. Since this formulation is well tolerated on the qodx5 schedule at 20 mg/kg, a dose of 20 mg/kg falls below the MTD. Dose escalation should increase the response rate.

Consistent with what was observed in the treatment with paclitaxel in 5% EVE on a qdx5 schedule, treatment with this formulation on a qodx5 schedule also resulted in more mice with transient partial tumor regression in sizes below that on Day 1 at both the 20 mg/kg and 15 mg/kg doses (6 in 10 mice). In comparison, treatment with Clinical Taxol and paclitaxel in 5% EC resulted in such partial tumor shrinkage in 3 and 5 mice, respectively.

Example 6
Safety of Vehicles containing Vitamin E-TPGS Delivered Orally

The safety of the orally delivered vehicles containing vitamin E-TPGS was tested on female nude mice ((NCr)-nufBr, Taconic Farms, Inc.). This information can be useful for guiding the design of oral formulations of paclitaxel containing vitamin E-TPGS.

1) Vehicle Combining Vitamin E-TPGS and PEG 300

PEG 300 was mixed with Vitamin E-TPGS (D-α-tocopheryl polyethylene glycol 1000 succinate) at 1:4 w/w ratio, and ascorbic acid at 1%. This vehicle is designated as "PVE". The PVE vehicle was diluted with D5W (5% dextrose in water at pH 4.8) to provide specified concentrations as listed in Tables 6 and 7 and volumes of 0.20 ml per 20-g mouse, body weight adjusted, were administered orally on a pdx5 schedule (once a day for 5 days) to groups of 5 mice. The concentration of ascorbic acid after the dilution with D5W ranged from 0.125% to 0.3%. Body weights of the treated mice were measured daily during dosing and twice weekly thereafter until the experiments were terminated on Day 20 or 22.

As shown in Tables 6 and 7 (shown in FIGS. 3 and 4, respectively), the PVE vehicle containing up to 6% PEG 300 was well tolerated by the nude mice. According to the definition by the NCI (the highest dose at which no more than 10% of the animals die and the group mean body-weight loss is no more than 20%), this dose is below the MTD of the vehicle. Overt toxic effects on the mice were not observed during the experiments.

2) Vehicle Combining Vitamin E-TPGS and Ethanol

Ethanol was mixed with Vitamin E-TPGS (D-α-tocopheryl polyethylene glycol 1000 succinate) at 1:1 w/w ratio, and ascorbic acid at 1%. This vehicle is designated as "EVE". The EVE vehicle was diluted with D5W to provide specified concentrations as listed in Tables 6 and 7 and volumes of 0.20 ml per 20-g mouse, body weight adjusted, were administered orally on a pdx5 schedule (once a day for 5 days) to groups of 5 mice. The concentration of ascorbic acid after the dilution with D5W ranged from 0.1% to 0.18%. Body weights of the treated mice were measured daily during dosing and twice weekly thereafter until the experiments were terminated on Day 20 or 22.

As shown in Tables 6 and 7, the EVE vehicle containing up to 16% ethanol was well tolerated by the nude mice, indicating that the dose is below the MTD of the vehicle. Overt toxic effects on the mice were not observed during the experiments.

What is claimed is:

1. A method for treating a disease associated with undesirable cell proliferation or angiogenesis in a patient suffering therefrom, comprising:

providing a water miscible, non-aqueous paclitaxel formulation comprising paclitaxel and ascorbic acid dissolved in a water-miscible non-aqueous solvent and a pharmaceutically-acceptable, water-miscible solubilizer selected from the group consisting of solubilizers having the general structures of $R_1COOR_2$, $R_1CONR_2$, and $R_1COR_2$, wherein $R_1$ is a derivative of d-α-tocopherol and $R_2$ is a hydrophilic moiety;

diluting the water miscible, non-aqueous paclitaxel formulation into a pharmaceutically acceptable aqueous solution; and parenterally administering to the patient the pharmaceutically acceptable aqueous solution comprising paclitaxel at a dose of 0.1–50 mg/Kg, wherein the said disease is sensitive to the effects of said non-aqueous paclitaxel formulation.

2. The method of claim 1, wherein the pharmaceutically acceptable aqueous solution is administered intravenously.

3. The method of claim 1, wherein paclitaxel is at a dose of 1–20 mg/Kg.

4. The method of claim 1, wherein paclitaxel is at a dose of 1–10 mg/Kg.

5. The method of claim 1, wherein paclitaxel is at a dose of 2–8 mg/Kg.

6. The method of claim 1, wherein paclitaxel is at a dose of 3–6 mg/Kg.

7. The method of claim 1, wherein the pharmaceutically acceptable aqueous solution is administered by infusion to the patient for less than 6 hours.

8. The method of claim 1, wherein the pharmaceutically acceptable aqueous solution is administered by infusion to the patient for less than 3 hours.

9. The method of claim 1, wherein the pharmaceutically acceptable aqueous solution is administered to the patient once every week.

10. The method of claim 1, wherein the pharmaceutically acceptable aqueous solution is administered to the patient once every two weeks.

11. The method of claim 1, wherein the pharmaceutically acceptable aqueous solution is administered to the patient once every three weeks.

12. The method of claim 1, wherein the solubilizer is d-α-tocopherol polyethylene glycol succinate.

13. The method of claim 12, wherein the d-α-tocopherol polyethylene glycol succinate is d-α-tocopherol polyethylene glycol 1000 succinate.

14. The method of claim 1, wherein the water-miscible non-aqueous solvent is an alcohol.

15. The method of claim 14, wherein the solvent is selected from the group consisting of ethanol, propylene glycol, benzyl alcohol, and polyethylene glycol (PEG).

16. The method of claim 1, wherein the solvent is an amide.

17. The method of claim 16, wherein the solvent is selected from the group consisting of 2-pyrrolidone, N-methyl-pyrrolidone and N,N-dimethyl acetamide.

18. The method of claim 13, wherein the weight ratio of d-α-tocopherol polyethylene glycol succinate to the solvent is between about 90:10 and 40:60.

19. The method of claim 13, wherein the weight ratio of d-α-tocopherol polyethylene glycol succinate to the solvent is between about 70:30 and 45:55.

20. The method of claim 13, wherein the weight ratio of d-α-tocopherol polyethylene glycol succinate to the solvent is between about 50:50.

21. The method of claim 1, wherein the water-miscible, non-aqueous paclitaxel formulation is diluted with infusion fluid to form the pharmaceutically acceptable aqueous solution.

22. The method of claim 1, wherein the amount of ascorbic acid in the paclitaxel formulation before the dilution is between about 0.1–5% w/w.

23. The method of claim 1, wherein the amount of ascorbic acid in the paclitaxel formulation before the dilution is between about 0.4–2% w/w.

24. The method of claim 1, wherein the amount of ascorbic acid in the paclitaxel formulation before the dilution is between about 0.5–1% w/w.

25. The method of claim 1, further comprising: administering to the patient a desensitizer that reduces allergic effects of the pharmaceutical composition on the patient.

26. The method of claim 25, wherein the desensitizer is a steroid, antihistamine or an H-2 receptor blocker.

27. The method of claim 26, wherein the steroid is selected from the group consisting of dexamethasone, prednisone and hydrocortisone.

28. The method of claim 26, wherein the antihistamine is diphenhydramine.

29. The method of claim 26, wherein the H-2 receptor blocker is cimetidine or ranitidine 30. The method of claim 25, wherein the desensitizer is administered to the patient prior to administration of the pharmaceutically acceptable aqueous solution.

31. The method of claim 1, further comprising: administering to the patient granulocyte-colony stimulating factor.

32. The method of claim 31, wherein granulocyte-colony stimulating factor is administered to the patient at least 24 hours after the administration of the pharmaceutical composition.

33. The method of claim 1, further comprising: administering to the patient an antineoplastic agent selected from the group consisting of an alkylating agent, antibiotic agent, antimetabolic agent, hormonal agent, plant-derived agent, and biologic agent.

34. The method of claim 33, wherein the alkylating agent is selected from the group consisting of bischloroethylamines, aziridines, alkyl alkone sulfonates, nitrosoureas, nonclassic alkylating agents and platinum compounds.

35. The method of claim 33, wherein the antibiotic agent is selected from the group consisting of doxorubicin, daunorubicin, epirubicin, idarubicin and anthracenedione, mitomycin C, bleomycin, dactinomycin, and plicatomycin.

36. The method of claim 33, wherein the antimetabolic agent is selected from the group consisting of fluorouracil, floxuridine, methotrexate, leucovorin, hydroxyurea, thioguanine, mercaptopurine, cytarabine, pentostatin, fludarabine phosphate, cladribine, asparaginase, and gemcitabine.

37. The method of claim 33, wherein the hormonal agent is selected from the group consisting of diethylstibestrol, tamoxifen, toremifene, fluoxymesterol, raloxifene, bicalutamide, nilutamide, flutamide, aminoglutethimide, tetrazole, ketoconazole, goserelin acetate, leuprolide, megestrol acetate and mifepristone.

38. The method of claim 33, wherein the plant-derived agent is selected from the group consisting of vincristine, vinblastine, vindesine, vinzolidine, vinorelbine, etoposide teniposide, camptothecin.

39. The method of claim 33, wherein the biologic agent is selected from the group consisting of immuno-modulating proteins, monoclonal antibodies against tumor antigens, tumor suppressor genes, and cancer vaccines.

40. The method of claim 39, wherein the immuno-modulating protein is selected from the group consisting of interleukin 2, interleukin 4, interleukin 12, interferon α, interferon β, interferon γ, erytbropoietin, granulocyte-CSF, granulocyte, macrophage-CSF, bacillus Calmette-Guerin, levamisole, and octreotide.

41. The method of claim 39, wherein the monoclonal antibody against tumor antigen is HERCEPTIN® (Trastruzumab), or RITUXAN® (Rituximab).

42. The method of claim 39, wherein the tumor suppressor gene is selected from the group consisting of DPC-4, NF-1, NF-2, RB, p53, WT1, BRCA, and BRCA2.

43. The method of claim 1, wherein the disease associated with undesirable cell proliferation or angiogenesis is selected from the group consisting of restenosis, benign tumors, malignant tumors and tumor metastasis, atherosclerosis, insults to body tissue due to surgery, abnormal wound healing, fibrosis of tissue, repetitive motion disorders, and proliferative responses associated with organ transplants.

44. A method for treating a disease associated with undesirable cell proliferation or angiogenesis in a patient suffering therefrom, comprising:
orally administering to the patient a water-miscible, non-aqueous pharmaceutical composition comprising paclitaxel at a dose of 0.1–100 mg/Kg, wherein the pharmaceutical composition further comprises ascorbic acid, both paclitaxel and ascorbic acid being dissolved in a water-miscible, non-aqueous solvent and a pharmaceutically-acceptable, water-miscible solubilizer selected from the group consisting of solubilizers having the general structures of $R_1COOR_2$, $R_1CONR_2$, and $R_1COR_2$, wherein $R_1$ is a derivative of d-α-tocopherol and $R_2$ is a hydrophilic moiety; and said disease is sensitive to the effects of said non-aqueous paclitaxel composition.

45. The method of claim 44, wherein the solubilizer is d-α-tocopherol polyethylene glycol succinate.

46. The method of claim 45, wherein the d-α-tocopherol polyethylene glycol succinate is d-α-tocopherol polyethylene glycol 1000 succinate.

47. The method of claim 44, wherein the pharmaceutical composition further comprises polyethylene glycol (PEG).

48. The method of claim 47, wherein said polyethylene glycol is PEG 300 or PEG. 400.

* * * * *